(12) United States Patent  
Maierhofer et al.

(10) Patent No.: US 11,529,450 B2  
(45) Date of Patent: Dec. 20, 2022

(54) DEVICE FOR EXTRACORPOREAL BLOOD TREATMENT HAVING AN EVALUATION AND CONTROL UNIT

(71) Applicant: FRESENIUS MEDICAL CARE DEUTSCHLAND GMBH, Bad Homburg (DE)

(72) Inventors: Andreas Maierhofer, Schweinfurt (DE); Wei Zhang, Niederwerrn (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1163 days.

(21) Appl. No.: 15/998,566

(22) PCT Filed: Feb. 15, 2017

(86) PCT No.: PCT/EP2017/000214  
§ 371 (c)(1),  
(2) Date: Aug. 15, 2018

(87) PCT Pub. No.: WO2017/140424  
PCT Pub. Date: Aug. 24, 2017

(65) Prior Publication Data  
US 2020/0276380 A1 Sep. 3, 2020

(30) Foreign Application Priority Data

Feb. 15, 2016 (DE) ...................... 10 2016 001 710.4

(51) Int. Cl.  
*A61M 1/36* (2006.01)

(52) U.S. Cl.  
CPC ... *A61M 1/3658* (2014.02); *A61M 2205/3334* (2013.01); *A61M 2205/3382* (2013.01);  
(Continued)

(58) Field of Classification Search  
CPC .............. A61M 1/3653; A61M 1/3655; A61M 1/3656; A61M 1/3658; A61M 2205/3334;  
(Continued)

(56) References Cited

U.S. PATENT DOCUMENTS 6,153,109 A 11/2000 Krivitski  
10,016,138 B2 7/2018 Zhang et al.  
(Continued)

FOREIGN PATENT DOCUMENTS

DE 19702441 2/1998  
DE 102012007081 10/2013  
(Continued)

OTHER PUBLICATIONS

Machine translation of WO 2011/131358 to Pfeiffer et al. (Year: 2011).*

(Continued)

*Primary Examiner* — Philip R Wiest  
(74) *Attorney, Agent, or Firm* — Jacobson Holman PLLC

(57) ABSTRACT

The invention relates to a blood treatment device having an extracorporeal blood circuit which comprises an arterial line, a blood pump, a blood treatment unit and a venous line, wherein the arterial and venous lines can be connected to a blood vessel of a patient, and wherein the blood treatment device has an evaluation and control unit, wherein the evaluation and control unit is configured to carry out the following steps: (a1) determining the blood recirculation in a blood vessel of the patient connected to the extracorporeal blood circuit; and (b) calculating the blood flow in the blood vessel using the blood recirculation determined in accordance with (a1) and using a provided value or a value likewise previously determined for the cardiac output of the patient.

9 Claims, 5 Drawing Sheets

Figure 1:
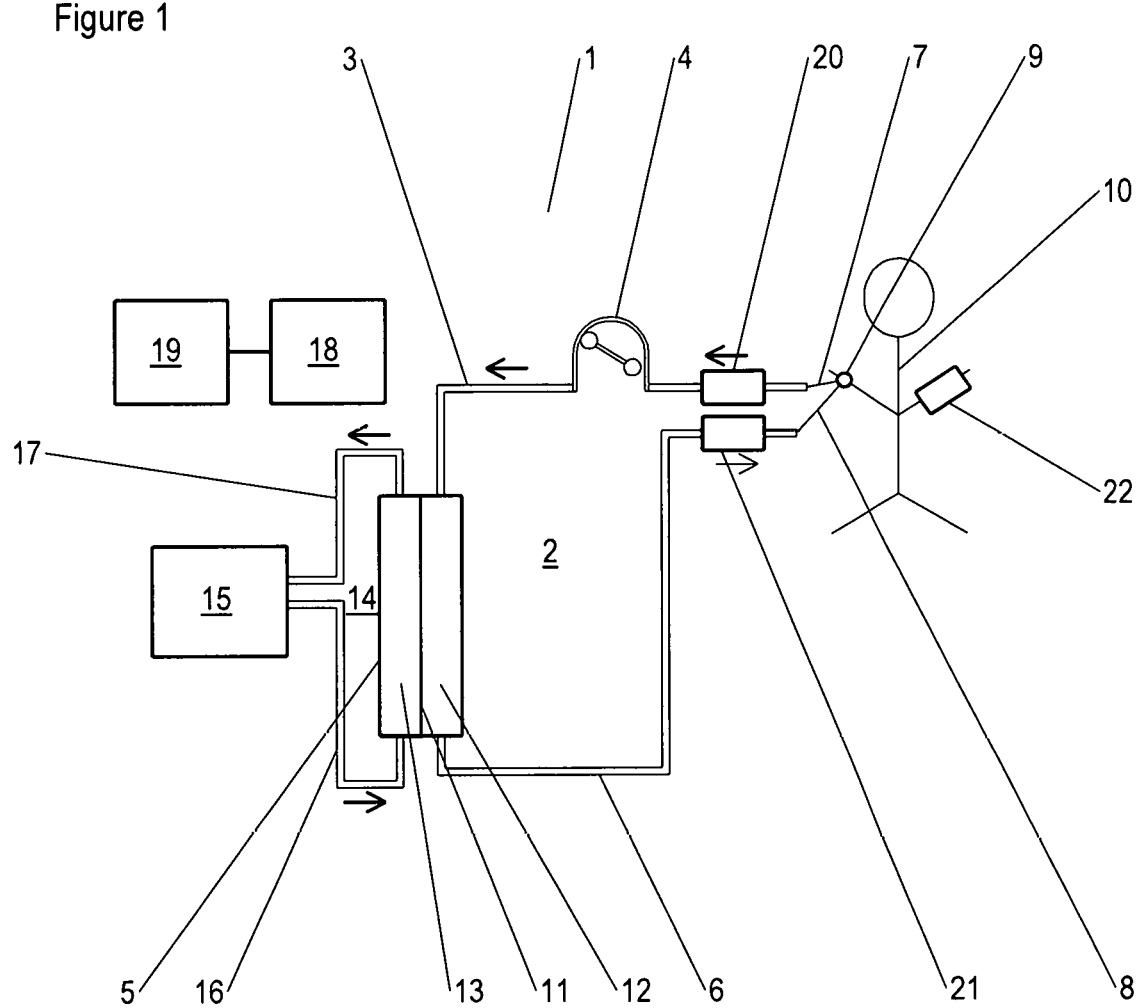

(52) U.S. Cl.
CPC . *A61M 2205/3386* (2013.01); *A61M 2230/30* (2013.01); *A61M 2230/50* (2013.01)

(58) Field of Classification Search
CPC .. A61M 2205/3382; A61M 2205/3386; A61M 2230/30; A61M 2230/50
See application file for complete search history.

(56) References Cited

U.S. PATENT DOCUMENTS

| | | | |
|---|---|---|---|
| 2005/0096578 | A1 | 5/2005 | Kleinekofort |
| 2009/0054822 | A1 | 2/2009 | Murakami et al. |
| 2011/0034813 | A1 | 2/2011 | Cohen et al. |
| 2013/0006130 | A1* | 1/2013 | Olde ................. A61B 5/026 600/504 |

FOREIGN PATENT DOCUMENTS

| | | |
|---|---|---|
| DE | 102013103218 | 10/2014 |
| EP | 0569506 | 10/1995 |
| EP | 0773035 | 9/2006 |
| EP | 1576341 | 2/2013 |
| WO | WO 2009/065611 | 5/2009 |
| WO | WO 2011/080194 | 7/2011 |
| WO | WO 2011/131358 | 10/2011 |

OTHER PUBLICATIONS

Schneditz et al. Measurement of Access Fiow During Hemodialysis Using the Constant Infusion Approach, ASAIO Journal 1998, pp. 74-81.

Schneditz et al. Surveillance of Access Function by the Blood Temperature Monitor. Seminars in Dialysis 16, Renal Research Institute Symposium, 2003, pp. 483-487.

* cited by examiner

DEVICE FOR EXTRACORPOREAL BLOOD TREATMENT HAVING AN EVALUATION AND CONTROL UNIT

The invention relates to a blood treatment device having an extracorporeal blood circuit which comprises an arterial line, a blood pump, a blood treatment unit and a venous line, wherein the arterial and venous lines can be connected to a blood vessel of a patient, and wherein the blood treatment device has an evaluation and control unit for determining the blood flow in the involved vessel of the patient.

The requirement for an efficient extracorporeal blood treatment, for example efficient dialysis, is the presence of a working vessel access.

An arteriovenous fistula is therefore frequently artificially established for the extracorporeal blood treatment, typically in the lower arm between the radial artery and the cephalic vein. The vessel pressure is increased by this short-circuiting of the artery and vein; it is caused by a reduced tissue resistance. A high blood flow in the involved vessel is thus achieved.

In order moreover to ensure a working vessel access, different methods are recommended in the relevant guidelines. They include the measurement of the recirculation on the removal from the vessel access and the determination of the flow in the vessel access such as is known from Schneditz et al. (1998): "*measurement of access flow during hemodialysis using the constant infusion approach*", ASAIO Journal 44, p. 74ff. However, only a very rough evaluation of the vessel access can be made on the basis of recirculation values. The measurement of the flow in the vessel access requires a temporary swapping over of the arterial and venous needles and a special disposable and actions of the user are required for this.

It is, for example, known in the prior art from WO 2011/131358 A2 to determine the fistula blood flow on the basis of dilution measurements. The patents EP 0 773 035 B2 and EP 1 576 341 B1 also deal with the subject of determining the fistula blood flow.

It is an object of the invention to provide a device for extracorporeal blood treatment which allows a simple and reliable measurement of the blood flow in the vessel access.

Against this background, the invention relates to a blood treatment device having an extracorporeal blood circuit which comprises an arterial line, a blood pump, a blood treatment unit and a venous line, wherein the arterial and venous lines can be connected to a blood vessel of a patient, and wherein the blood treatment device has an evaluation and control unit. In accordance with the invention, the blood treatment device is characterized in that the evaluation and control unit is configured to carry out the following steps: (a1) determining the blood recirculation in a blood vessel of the patient connected to the extracorporeal blood circuit; and (b) calculating the blood flow in the blood vessel using the blood recirculation determined in accordance with (a1) and using a provided value or a value likewise previously determined for the cardiac output of the patient.

The blood treatment device can, for example, be a dialysis machine or an apheresis machine. The blood treatment unit can, for example, be a dialyzer or a plasma filter.

In an embodiment, the blood treatment device furthermore has a blood pressure sensor and the evaluation and control unit is configured furthermore to carry out the following step prior to step (b): (a2) determining the cardiac output of the patient by evaluating the time progression of a pressure pulse measured using the blood pressure sensor. The blood pressure sensor can furthermore be suitable to measure the blood pressure directly at the patient, for example at the patient's arm or wrist. Suitable pressure sensors comprise piezoelectric pressure sensors.

Provision can therefore be made within the framework of the invention that the cardiac output is determined from oscillometric blood pressure measurements. The evaluation of such oscillometric blood pressure measurements is known, for example, for determining the blood pressure (cf. DE 10 2012 007 081 A1).

Methods based on pulse analysis for determining the cardiac output are known in the prior art. All these methods use pulse curves to determine the cardiac output. The evaluation and control unit of the blood treatment device in accordance with the invention can be configured to determine the cardiac output using such a method based on pulse analysis and then to use it in step (b).

Suitable methods based on pulse analysis comprise the impulse response method, which is described in more detail, for example, in US 2011/0034813 A1, or the model flow method which is described in more detail in EP 0 569 506 B1.

The determination of the cardiac output from the mean arterial blood pressure, the central nervous pressure and the peripheral resistance is preferred such as is used in the commercially available "Vicorder" device of the company SMT medical GmbH.

In an embodiment, the blood treatment device furthermore has a bolus sensor arranged in the arterial line of the extracorporeal blood circuit and the evaluation and control unit is configured to carry out step (a1) in the following manner: (a1) determining the blood recirculation in a blood vessel of the patient connected to the extracorporeal blood circuit using the signal of the bolus sensor.

In an embodiment, the blood treatment device has a control unit and an actuator, wherein the actuator is configured such that a bolus administration can take place downstream of a blood pump arranged in the extracorporeal blood circuit and/or downstream of the blood treatment unit, and wherein the control unit is configured such that a bolus administration takes place once or a plurality of times when using the actuator during a measurement interval. The actuator can, for example, be a heating with which a temperature bolus can be produced. The actuator can furthermore be a metering system which opens into the extracorporeal blood circuit and with which a concentration bolus or temperature bolus can be produced.

The blood treatment device furthermore preferably has a bolus sensor arranged in the venous line of the extracorporeal blood circuit, wherein the evaluation and control unit is configured to determine the blood recirculation in the vessel section of the patient while using the signals of the arterial and venous bolus sensor. Provision can in particular be made that the evaluation and control unit in this respect takes account of the similarity of the signal progressions and the time offset of the signals obtained from the different sensors.

The bolus sensor or sensors can be temperature sensors to recognize a temperature bolus.

The measurement of the recirculation between the venous and arterial needles by means of thermodilution is described, for example, in Schneditz et al. (2003), "*Surveillance of Access Function by the Blood Temperature Monitor*", Seminars in Dialysis 16, p. 483ff. In this respect, a temperature bolus is produced at the blood side downstream of the dialyzer and is detected by a sensor system at the venous and arterial hose systems. The recirculation is calculated by the comparison of the temperature boli measured at the venous and arterial sides. The specified measurement accuracy amounts to ±2%. The interpretation of the values takes place without considering vital parameters of the patient or treatment parameters. Values <10% are thus generally considered as a normal cardiopulmonary recirculation, whereas larger values are evaluated as indications of the presence of recirculation in the vessel access, e.g. due to a swapping over of the arterial and venous needles.

In an embodiment, the evaluation and control unit is configured furthermore to take account of the extracorporeal blood flow and the outflow of fluid in the blood treatment device, in addition to the blood recirculation and the cardiac output, when determining the blood flow in step (b). The extracorporeal blood flow $Q_b$ can be set, for example, by setting the conveying rate of a blood pump present in the arterial line. The outflow of fluid in the blood treatment device can in particular be the ultrafiltration rate. It can be set, for example, using a UF pump which is arranged in a dialysis fluid system likewise connected to the dialyzer.

In an embodiment, the evaluation and control unit is configured to define critical values for the recirculation for a normal and/or inverse connection of the arterial and venous lines to the blood vessel under the assumption that the blood flow in the corresponding vessel can achieve a specific portion of the cardiac output as a maximum. The maximum portion in the cardiac output which the blood flow can reach as a maximum in the corresponding vessel can be 50%, for example. Critical values for the recirculation can thus be defined at normal and inverse needle positions. The critical values differ depending on the flow in the extracorporeal blood circuit.

In an embodiment, the evaluation and control unit is configured to compare the determined recirculation with these critical values and to group them on the basis of the comparison.

In an embodiment, the device furthermore has an output unit which communicates with the evaluation and control unit, wherein the output unit and the evaluation and control unit are configured to output a different signal to the user depending on the group association of the determined recirculation. The output unit can, for example, output acoustic and/or visual signals to the user.

In an embodiment, three groups are distinguished: (1) the determined recirculation is below the critical values for a normal connection; (2) the determined recirculation is above the critical values for a normal connection, but below the critical value for an inverse connection; and (3) the determined recirculation is above the critical value for an inverse connection.

With respect to the signal output, when the determined recirculation can be associated with group (1), for example, a signal can be output which is indicative of a correct connection of the extracorporeal blood circuit to the vessel and/or, when the determined recirculation can be associated with group (3), a signal can be output which is indicative of a swapping over of the arterial and venous connections.

In an embodiment, the evaluation and control unit is configured such that, when the determined recirculation has been associated with group (2), the conveying performance of the blood pump is reduced and the carrying out of steps (a1) and (b) is repeated.

In an embodiment, the evaluation and control unit is configured to output a warning signal when the determined blood flow in the corresponding blood vessel exceeds an upper threshold vale or falls below a lower threshold value.

In this case, a check of the value determined in accordance with the invention by swapping over the arterial and venous needles and a use of an already known method can be indicated. The lower threshold value can, for example be 300 or 500 ml/min; and the upper threshold value can, for example, be 2000 or 1500 ml/min.

The evaluation and control unit can preferably initiate interventions in the dialysis device required for the data collection (e.g. operation of the blood pump at a specific rate or administration of a temperature bolus). It can be configured such that the determined data or conclusions (e.g. the blood flow in the respective vessel, correct or inverse connection of the needle, signals with respect to a correct access, etc.) are automatically used to control the device.

In an embodiment, the blood treatment device has an acoustic and/or visual output unit by which the data or conclusions (see above) determined by the evaluation unit are output to a user.

The invention furthermore comprises a method of determining the blood flow in a blood vessel of a patient connected to the extracorporeal blood circuit of a blood treatment device, preferably a blood treatment device in accordance with the invention. Provision is made in this respect to determine the recirculation in the vessel and to determine the blood flow in the respective blood vessel of the patient using this recirculation and a value for the cardiac output likewise determined or estimated in another manner as the basis.

In addition to the initially named object, it is furthermore an object of the invention to provide a device for extracorporeal blood treatment which allows a determination of the quality of the vessel access.

In this connection, the invention relates to a blood treatment device having an extracorporeal blood circuit which comprises an arterial line, a blood pump, a blood treatment unit and a venous line, wherein the arterial and venous lines can be connected to a blood vessel of a patient, and wherein the blood treatment device has an evaluation and control unit. Provision is made in accordance with the invention that the evaluation and control unit is configured to determine the blood recirculation in a blood vessel of the patient connected to the extracorporeal blood circuit and to compare the determined recirculation with critical values likewise determined or predefined and to group it on the basis of the comparison. A grouping of the recirculation values therefore takes place here optionally without determining the blood flow in the blood vessel.

The determination of the blood recirculation can in this respect take place as described above.

The device can here furthermore also have an output unit which communicates with the evaluation and control unit, wherein the output unit and the evaluation and control unit are configured to output a different signal to the user depending on the group association of the determined recirculation. The output can in this respect take place as described above.

Alternatively or in addition to the output to the user, a response of the blood treatment device can be initiated.

Three groups can also be distinguished here analog to the first embodiment of the invention: (1) the determined recirculation is below the critical value for a normal connection; (2) the determined recirculation is above the critical value for a normal connection, but below the critical value for an inverse connection; and (3) the determined recirculation is above the critical value for an inverse connection.

Likewise analog to the first embodiment of the invention, the evaluation and control unit can be configured such that, when the determined recirculation has been associated with group (2), the conveying performance of the blood pump is reduced and the determination of the blood recirculation is repeated.

Finally, the invention furthermore comprises a method of determining the quality of the vessel access in a blood vessel of a patient connected to the extracorporeal blood circuit of a blood treatment device, preferably a blood treatment device in accordance with the invention. Provision is made in this respect to determine the recirculation in the vessel, to compare the determined recirculation with critical values likewise determined or predefined and to group it on the basis of the comparison.

Figure 2:
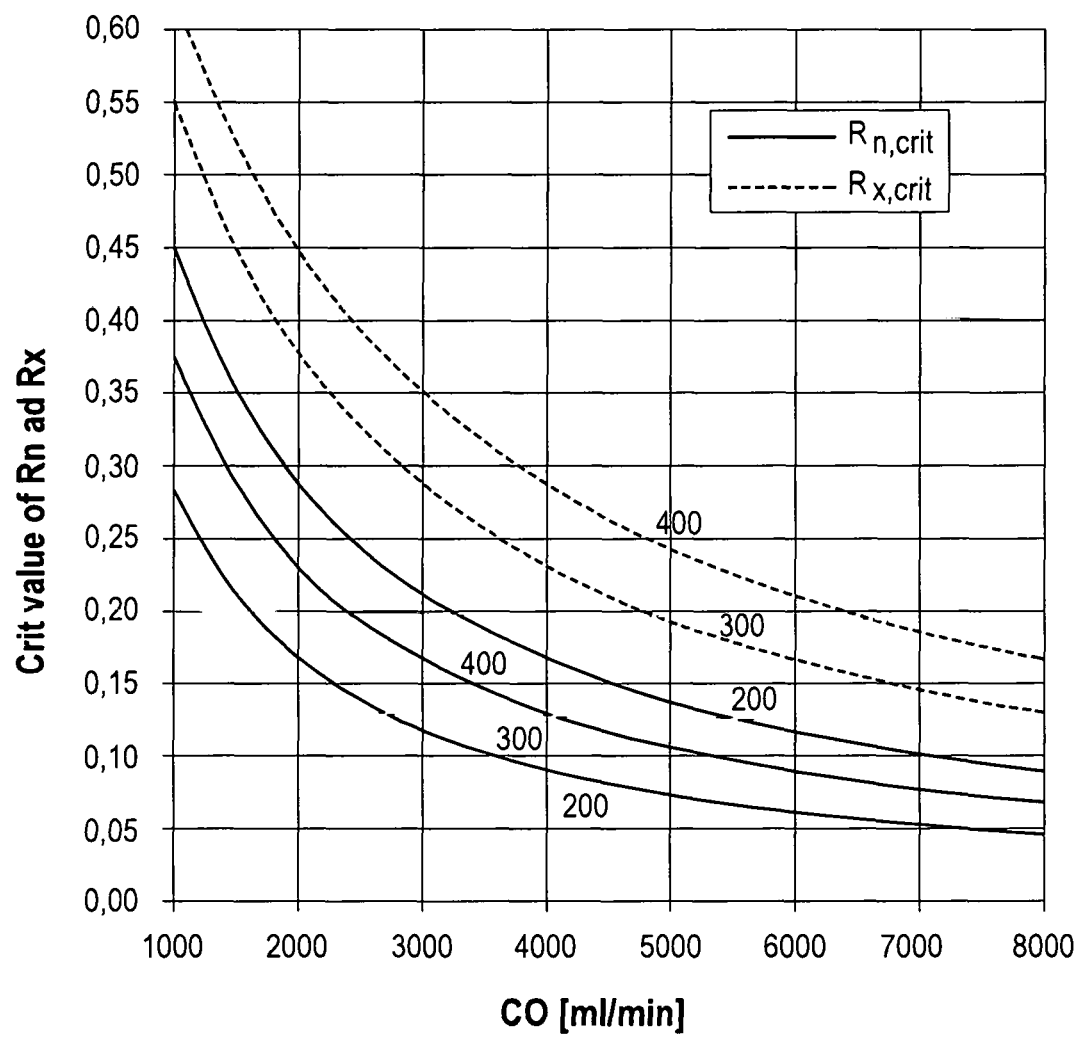
Figure 3:
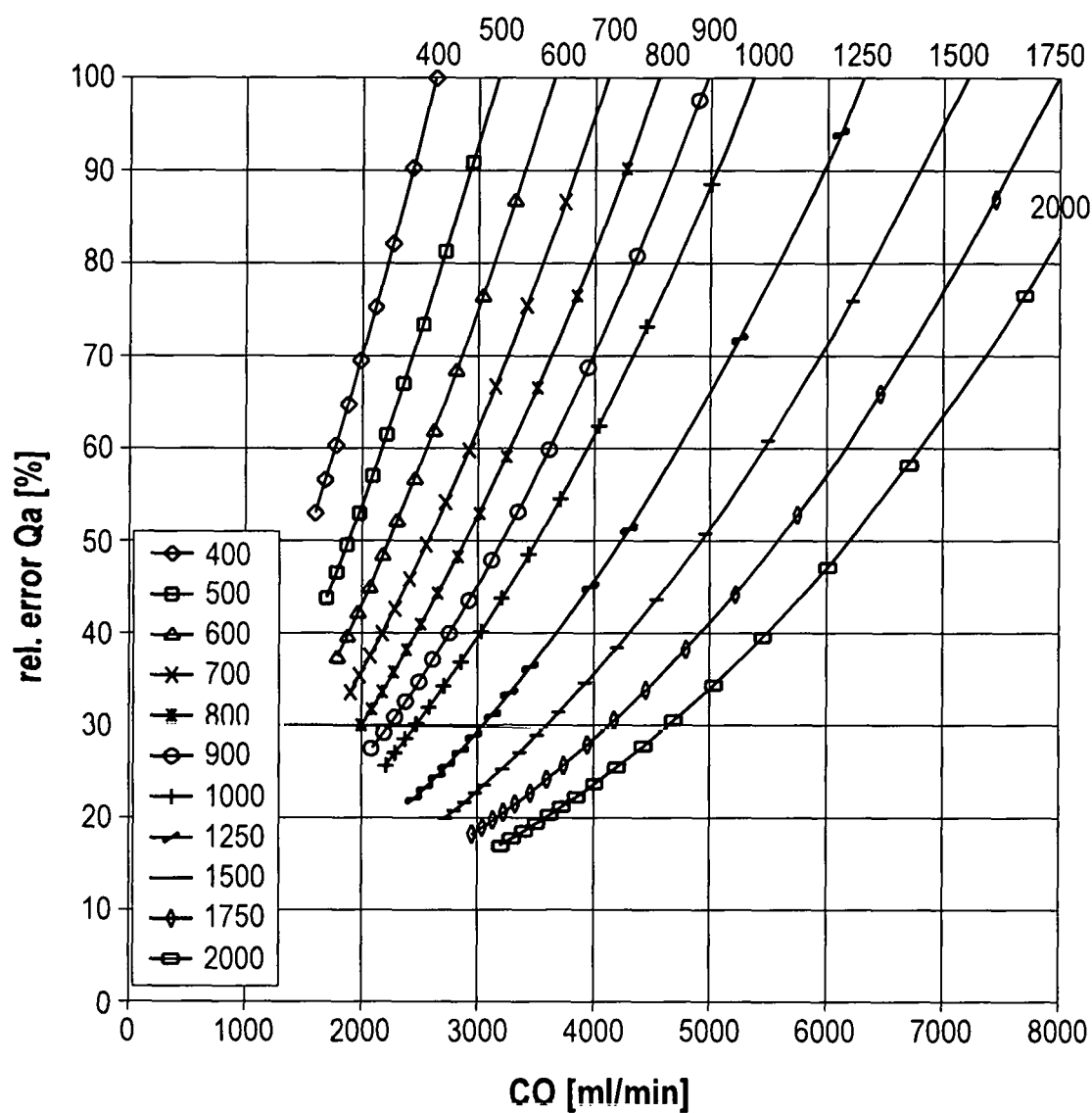
Figure 4:
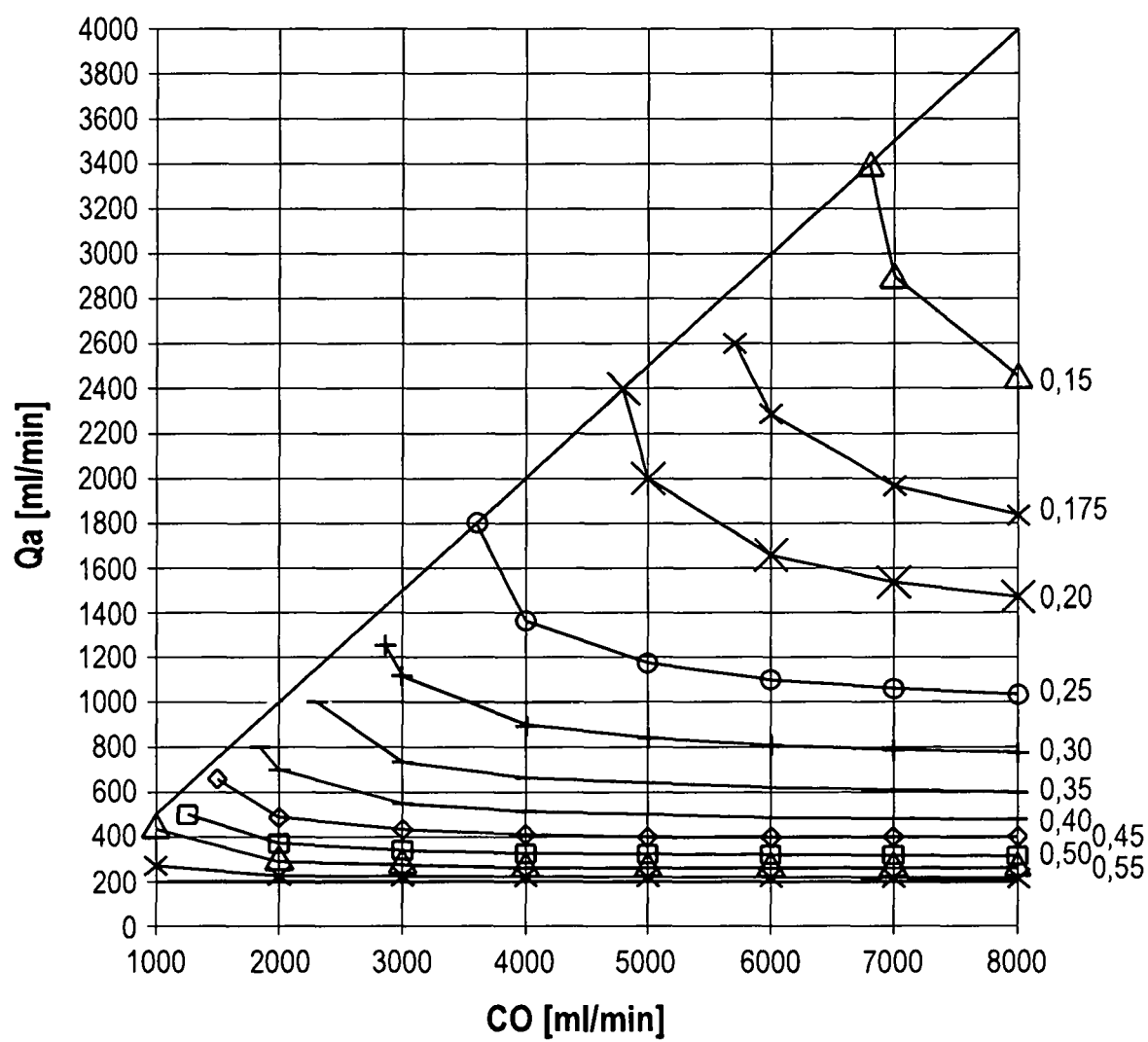
Figure 5:
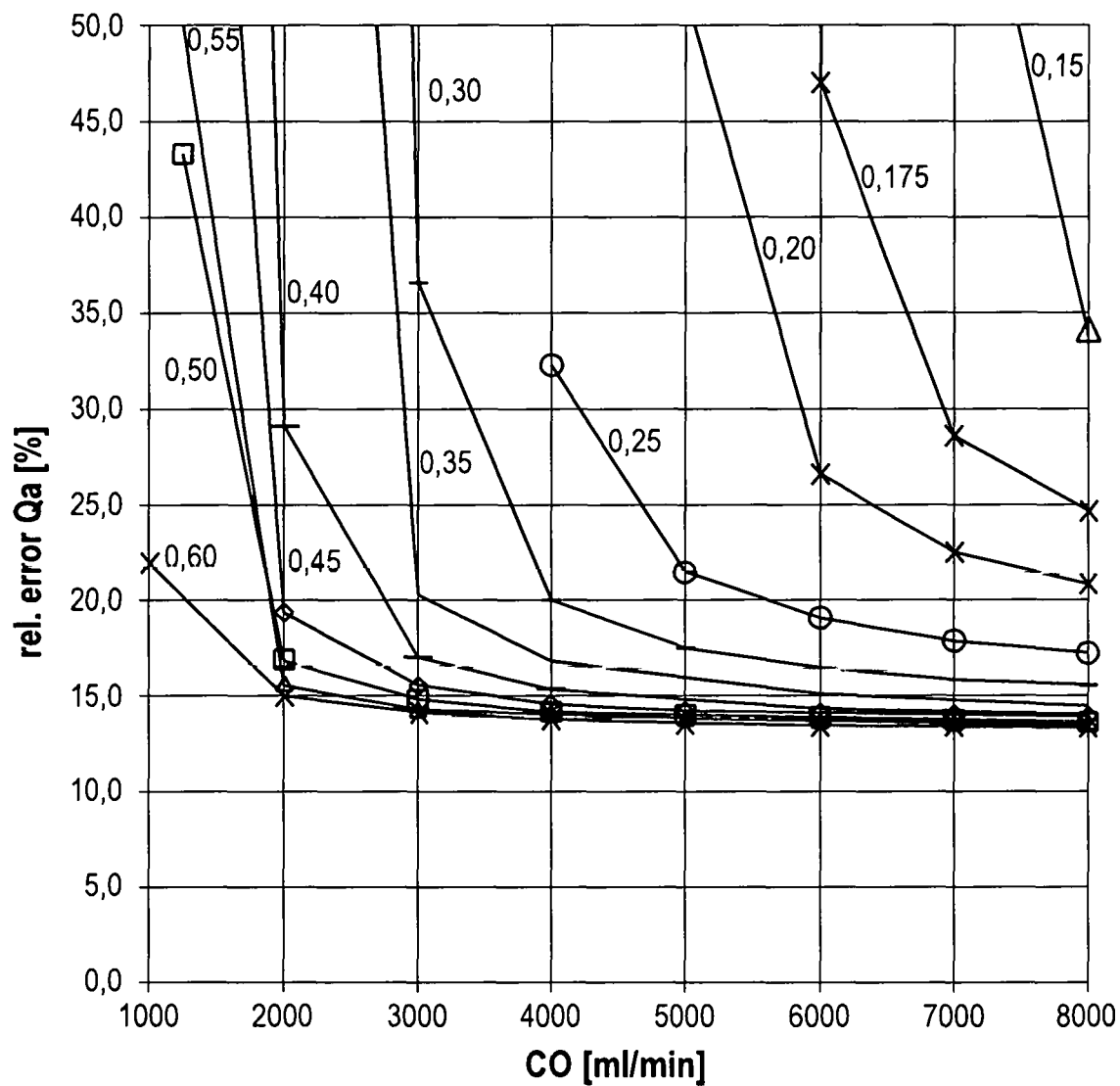

Further details and advantages of the invention result from the following embodiment shown with reference to the Figures. There are shown in the Figures:

FIG. 1: a schematic representation of an embodiment of a dialysis device in accordance with the invention;

FIG. 2: a plot of critical values determined in accordance with the invention for the portion of recirculations $R_n$ and $R_x$ in a normal and inverse needle position in dependence on the cardiac output CO for extracorporeal blood flows of 200, 300 and 400 ml/min;

FIG. 3: a plot of the relative error on the determination in accordance with the invention of the shunt flow $Q_a$ at a blood flow of 300 ml/min for values of $Q_a$ of 400 to 2000 ml/min;

FIG. 4: a plot of the shunt flow $Q_a$ in dependence on CO at different values of the recirculation $R_x$ in an inverse needle position at an extracorporeal blood flow of 300 ml/min; and FIG. 5: a plot of the relative error on the determination of the shunt flow $Q_a$ with swapped over needles and with an extracorporeal blood flow of 300 ml/min.

THEORETICAL BACKGROUND

The algorithm stored in the control unit of the dialysis device in accordance with the invention in accordance with the embodiment is based on the theoretical background explained below.

The cardiopulmonary recirculation in hemodialysis patients with a cardiac output CO who are treated via a vessel access with a shunt flow $Q_a$ is defined as $$CPR = \frac{Q_a}{CO} \quad \text{Formula 1}$$

According to Schneditz (1998), the shunt flow $Q_a$ can be determined with a known extracorporeal blood flow $Q_b$ and a UF rate $O_f$ by measuring the portion of recirculations $R_n$ and $R_x$ in a normal and inverse needle position. The following parameters are defined for this.

$$f_n = \frac{R_n}{1-R_n}, \; f_x = \frac{R_x}{1-R_x}, \; \tilde{Q} = Q_b - Q_f \quad \text{Formula 2}$$

The formula given by Schneditz (1998) herewith reads:

$$Q_a = \frac{1}{f_x}\frac{\tilde{Q}}{1-CPR} \; mit \; CPR = \frac{f_n}{f_x}\frac{\tilde{Q}}{Q_b} \quad \text{Formula 3}$$

If the cardiac output is known $Q_a$ can be calculated with knowledge of only one of the values $R_n$ or $R_x$.

$$Q_a = CO - \frac{\tilde{Q}}{f_n} \quad \text{Formula 4}$$

$$Q_a = \frac{CO}{2} - \sqrt{\left(\frac{CO}{2}\right)^2 - \frac{\tilde{Q}^2}{Q_b}\frac{CO}{f_x}} \quad \text{Formula 5}$$

The error of the determination of $Q_a$ from CO and $R_n$ can be estimated as follows according to the law of error propagation.

$$\sigma_{Q_a} = \sqrt{\sigma_{CO}^2 + \frac{(1-R_n)^2}{R_n^2}\sigma_{\tilde{Q}}^2 + \left(\frac{\tilde{Q}}{R_n^2}\right)^2\sigma_{R_n}^2} \quad \text{Formula 6}$$

$$\sigma_{Q_a} = \frac{1}{2}\left[\left(1 - \frac{\frac{1}{2}CO - \frac{(1-R_x)\tilde{Q}}{R_x}}{W}\right)^2 \sigma_{CO}^2 + \sqrt{\left(\frac{(1-R_x)CO}{R_x W}\right)^2 \sigma_{\tilde{Q}}^2 + \left(\frac{\tilde{Q}CO}{R_x^2 W}\right)^2 \sigma_{R_x}^2}\right] \quad \text{Formula 7}$$

$$mit \; W = \sqrt{\left(\frac{CO}{2}\right)^2 - \frac{\tilde{Q}CO}{f_x}}$$

It follows from formula 4 or formula 5.

$$R_n = \frac{\tilde{Q}}{\tilde{Q} + CO - Q_a}, \; R_x = \frac{\frac{\tilde{Q}^2}{Q_b}}{\frac{\tilde{Q}^2}{Q_b} + Q_a - \frac{Q_a^2}{CO}} \quad \text{Formula 8}$$

Under the physiologically founded assumption that the shunt flow $Q_a$ can reach as a maximum 50% of the cardiac output CO, critical values result for $R_n$ and $R_x$ which cannot be exceeded or fallen below in a measurement of the recirculation.

$$R_{n,crit} = \frac{1}{1+\frac{1}{2}\frac{CO}{\tilde{Q}}}, \; R_{x,crit} = \frac{1}{1+\frac{1}{4}\frac{Q_b}{\tilde{Q}^2}CO} \quad \text{Formula 9}$$

The measurement of the shunt flow is desired for various reasons. It is also important to recognize dangerously high shunt flows (steal syndrome) in addition to low shunt flows. In accordance with the present idea, the shunt flow $Q_a$ is therefore calculated as $Q_a = CO - Q_b/f_n$, where $f_n = R_n/1 - R_n$. R is the recirculation fraction here and $Q_b$ the extracorporeal blood flow. The cardiac output CO and the recirculation are determined experimentally. Dangerously high shunt flows can thus be recognized without disposable and without any intervention of the user. The concept also manages without the introduction of a bolus in one embodiment. With swapped over needles, a more accurate determination is also conceivable with low shunt flows due to the higher recirculation.

The determination of the cardiac output can, for example, take place using the formula $$CO = (MAP-CVP)/R_P,$$

where MAP is the mean arterial blood pressure, CVP is the central venous pressure and $R_P$ is the peripheral resistance. This method, which works according to the principle of "flow=pressure/resistance", is used, for example, in the commercial available Vicorder devices of the company SMT medical GmbH. The central venous pressure can in this respect, for example, be measured or estimated using a central venous catheter and can be input manually and the peripheral resistance can be determined from the falling flank of a pulse curve.

EMBODIMENT

A schematic representation of an embodiment of a dialysis device in accordance with the invention is shown in FIG. 1.

The dialysis device is generally marked by the reference numeral 1 in the Figure. It has an extracorporeal blood circuit 2 which comprises in a known manner an arterial line 3 having a blood pump 4, a dialyzer 5 and a venous line 6. The arterial line 3 and the venous line 6 are connected to a vessel 9 of a patient 10 by an arterial needle 7 or by a venous needle 8.

A semipermeable membrane 11 which separates the blood chamber 12 from the dialyzing fluid chamber 13 within the dialyzer 5 is arranged within the dialyzer 5. The arterial and venous lines 3 and 6 of the extracorporeal blood circuit 2 are connected to the blood chamber 12. A dialyzing fluid system 14 is connected to the dialyzing fluid chamber 13 and comprises an apparatus 15 for preparing a dialyzing fluid, a feed line 16 to the dialyzer 5 and an out line 17 from the dialyzer 5. An ultrafiltration pump, not shown in the Figure, can be arranged in the out line 17.

The directions of flow of the blood in the extracorporeal blood circuit 2 and of the dialyzing fluid in the dialyzing fluid system 14 are shown by arrows in the Figure.

The dialysis device 1 furthermore comprises an evaluation and control unit 18 and an output unit 19.

Temperature sensors 20 and 21 respectively are arranged close to the respective needles both at the arterial line 3 and at the venous line 6.

The device 1 furthermore comprises means, not shown in the Figure, for varying the blood temperature in the venous blood line. These means can, for example, comprise the temperature of the dialyzing fluid produced in the apparatus 15 being varied according to the demand of the evaluation and control unit 18 with the aim of a change in the blood temperature. Alternatively, the change in the blood temperature can e.g. also take place by Peltier elements attached to the blood hose system.

Finally, the device 1 comprises a sensor 22 to measure a pulse pressure curve progression of the patient which is suitable to determine CO, e.g. by a cuff on the upper arm. The sensor is connected to the control and evaluation unit 18 in a manner not shown in the Figure.

In operation of the apparatus, the blood pump 4 sucks in blood from the vessel 9 of the patient via the arterial needle 7 into the arterial line 3 of the extracorporeal blood circuit 2 and subsequently pumps the blood through the dialyzer 5, the venous line 6 and the venous needle 8 back into the vessel 9 of the patient 10. After administering a temperature bolus, the temporal temperature progression of the removed and returned blood is measured at the sensors 20 and 21 and the measured values are transferred to the evaluation and control unit 18. The recirculation R is then determined in the evaluation and control unit 18 as described in Schneditz (2003). Furthermore, the cardiac output is determined by means of oscillometric blood pressure measurements at the blood pressure sensor.

Alternatively, the cardiac output can be estimated with a known stroke volume $V_{co}$ originating, for example, from echocardiogram examinations or estimated as a typical value of 70 ml, by measuring the heart rate v, by means of $CO = v \cdot V_{co}$.

After determining R and CO and with a known conveying rate of the blood pump 4 and ultrafiltration rate, the calculations presented above in more detail are now carried out in the evaluation and control unit 18 for determining the blood flow in the vessel 9 of the patient 10. The results can, for example, be output at the output unit 19, can be transferred via any desired manner of communication such as via a network, and/are can be used automatically for the control of the device 1.

Interpretation and Use of the Results:

The results can be interpreted or used in the manner described in the following.

If the cardiac output CO is measured or estimated close in time to the measurement of the recirculation R, critical values $R_{n,crit}$ and $R_{x,crit}$ for the recirculations $R_n$ and $R_x$ can be calculated in accordance with formula 9 in normal and inverse needle positions together with the known values for the extracorporeal blood flow and the UF rate, and R can be compared with these values. FIG. 2 shows the critical values for $R_n$ and $R_x$ calculated according to formula 9 in dependence on the cardiac output CO for extracorporeal blood flows of 200, 300 and 400 ml/min.

The critical values can, however, also be determined or predefined in another manner in a further embodiment of the invention.

Different cases can be distinguished which allow different conclusions.

If $R < R_{n,crit}$, only cardiopulmonary recirculation is present. The shunt flow is therefore larger than the extracorporeal blood flow; the arterial and venous needles are correctly punctured and connected to the hose system. The user can be informed of this in any desired manner by means of the output unit 19.

The shunt flow $Q_a$ can furthermore be estimated using formula 4. FIG. 3 shows the relative error in the determination of $Q_a$ calculated according to formula 6 with a blood flow of 300 ml/min under the assumption of an error in the recirculation measurement of ±1% and the determination of CO and of $Q_b$ of ±10% for values of $Q_a$ of 400 to 2000 ml/min. It becomes clear from this that the measurement accuracy is very restricted with low $Q_a$ values. It is nevertheless ensured that $Q_a > Q_b$ in every case. Since the relative error for high shunt flows falls, the determination of $Q_a$ can be used to be able to recognize dangerously high shunt flows. Shunt flows >2000 ml/min put a strain on the heart of the patient, which results in increased mortality. At the same time, they result in a lack of circulation of the limbs distal of the vessel access (typically close to the wrist), i.e. in particular of the hand and fingers, which can result in damage to them and in impairments of the patient. A warning of too high a shunt flow can therefore be generated on the basis of a shunt flow determined from $R_n$ and CO. If too low a shunt flow of <600 ml/min or too high a shunt flow is detected using the described method, the user can be prompted now to swap over the needles for a more accurate determination of the shunt flow, which is advantageously then easily possible if a disposable is already present for this purpose. $Q_a$ can then be determined more accurately in accordance with formula 3 from the determination of $R_x$; the determination of $R_n$ and CO would then only serve as pre-screening.

If $R>R_{x,crit}$, the vessel recirculation is so high that a swapping over of the arterial and venous needles is likely with a high probability. The user can also be informed of this in any desired manner by means of the output unit 19.

FIG. 4 shows a plot of the shunt flow $Q_a$ in dependence on CO at different values of $R_x$ in accordance with formula 5 with an extracorporeal blood flow of 300 ml/min. It can be recognized from this that the shunt flow can be determined solely from the measured recirculation $R_x$ with swapped over needles, in particular at low shunt flows (<800 ml/min) and that the value of the CO only slightly influences the value of the shunt flow when $Q_a<\frac{1}{4}$ CO. This can also be recognized in FIG. 5 where the relative error in the determination of $Q_a$ in accordance with formula 7 was plotted with an extracorporeal blood flow of 300 ml/min. The shunt flow can thus be determined solely by measurement of the recirculation with swapped over needles with only an imprecise knowledge of CO without requiring a recirculation measurement in a normal needle orientation. The time required for determining the shunt flow can thus be considerably reduced. The needle swapping generally has to take place manually by the user while using a corresponding disposable. In the event of an already incorrectly present needle swapping, the shunt flow can immediately be given by means of formula 5 once a needle swap has been recognized from the measurement of the recirculation and of the CO.

If $R_{n,crit}<R<R_{x,crit}$, there is a partial recirculation between the arterial and the venous needle, which can arise due to an unfavorable positioning of the needles (e.g. too close to one another). Alternatively, the extracorporeal blood flow can exceed the shunt flow. Provision can be made that the evaluation and control unit 18 is configured for distinguishing these two scenarios such that a recirculation measurement is carried out automatically with a reduced blood flow $Q_b'$ and the values are determined again. If the value R' then determined is below $R'_{n,crit}$, $Q_a$ is between $Q_b'$ and $Q_b$.

It results in summary that the present invention provides a possibility of recognizing a shunt flow which is above all excessively high. A very high shunt flow is medically undesirable. In accordance with the invention, the recirculation is determined, for example, by administering a temperature bolus and the cardiac output is determined, for example, by an oscillometric blood pressure measurement. The shunt flow is calculated from both using formula 4. Said shunt flow can above all be determined with a relatively small error at very high flows. The invention furthermore allows the determination of two limit values of the recirculation and the derivation of corresponding conclusions. A further aspect of the invention in particular deals with the comparison of the recirculation with limit values and with the derivation of conclusions in isolation from how the limit values are determined.

The invention claimed is:

1. A blood treatment device comprising:
an extracorporeal blood circuit, which includes an arterial line, a blood pump, a blood treatment unit, and a venous line, the arterial and venous lines being connectable to a blood vessel of a patient, and
an evaluation and control unit,
the evaluation and control unit being configured to carry out the following steps:

(a1) determining a blood recirculation in a blood vessel of the patient connected to the extracorporeal blood circuit;

(b) calculating a blood flow in the blood vessel using the blood recirculation determined in accordance with (a1) and using a provided value or a value likewise previously determined for a cardiac output of the patient; and accounting for an extracorporeal blood flow and an outflow of fluid in the blood treatment device, in addition to the blood recirculation and the cardiac output, when determining the blood flow in step (b) for controlling operation of the blood treatment device.

2. The blood treatment device in accordance with claim 1, further comprising a blood pressure sensor; wherein the evaluation and control unit is configured to carry out the following step:

(a2) determining the cardiac output of the patient by evaluating a time progression of a pressure pulse measured using the blood pressure sensor.

3. The blood treatment device in accordance with claim 1, further comprising a bolus sensor arranged in the arterial line of the extracorporeal blood circuit; wherein the evaluation and control unit is configured to carry out step (a1) in the following manner:

(a1) determining the blood recirculation in a blood vessel of the patient connected to the extracorporeal blood circuit using a signal of the bolus sensor.

4. The blood treatment device in accordance with claim 1, wherein the evaluation and control unit is configured to define critical values for the recirculation for a normal and/or inverse connection of the arterial and venous lines to the blood vessel under an assumption that the blood flow in a corresponding vessel can achieve a specific portion of the cardiac output as a maximum.

5. The blood treatment device in accordance with claim 4, wherein the evaluation and control unit is configured to compare the determined recirculation with the critical values and to group the recirculation values based on the comparison.

6. The blood treatment device in accordance with claim 5, further comprising an output unit which communicates with the evaluation and control unit, wherein the output unit and the evaluation and control unit are configured to output a different signal to a user depending on the group association of the determined recirculation.

7. The blood treatment device in accordance with claim 5, wherein three groups are distinguished:
(1) the determined recirculation is below the critical values for a normal connection;
(2) the determined recirculation is above the critical value for a normal connection, but below the critical value for an inverse connection; and
(3) the determined recirculation is above the critical value for an inverse connection.

8. The blood treatment device in accordance with claim 7, wherein the evaluation and control unit is configured such that, when the determined recirculation has been associated with group (2), a conveying performance of the blood pump is reduced and the carrying out of steps (a1) and (b) is repeated.

9. The blood treatment device in accordance with claim 1, wherein the evaluation and control unit is configured to output a warning signal when the calculated blood flow in a respective vessel exceeds an upper threshold value or falls below a lower threshold value.

* * * * *